(12) United States Patent
Albrecht

(10) Patent No.: US 6,172,046 B1
(45) Date of Patent: Jan. 9, 2001

(54) COMBINATION THERAPY FOR ERADICATING DETECTABLE HCV-RNA IN PATIENTS HAVING CHRONIC HEPATITIS C INFECTION

(75) Inventor: Janice K. Albrecht, Winter Park, FL (US)

(73) Assignee: Schering Corporation, Kenilworth, NJ (US)

(*) Notice: Under 35 U.S.C. 154(b), the term of this patent shall be extended for 0 days.

(21) Appl. No.: 08/938,033

(22) Filed: Sep. 21, 1997

(51) Int. Cl.$^7$ .......................... A61K 31/70; A01N 43/04
(52) U.S. Cl. .............................. 514/43; 514/42; 514/894; 424/85.4; 424/85.7
(58) Field of Search ............................... 514/42, 43, 894; 424/85.4, 85.7

(56) References Cited

U.S. PATENT DOCUMENTS

| | | | |
|---|---|---|---|
| Re. 29,835 | 11/1978 | Witlowski et al. | 536/29 |
| 4,211,771 | 7/1980 | Witlowski et al. | 424/180 |
| 4,530,901 | 7/1985 | Weissmann | 435/70 |
| 5,503,828 | 4/1996 | Testa et al. | |
| 5,767,097 | 6/1998 | Tam | |

FOREIGN PATENT DOCUMENTS

| | | |
|---|---|---|
| 0707855 | 4/1996 | (EP). |
| WO96/36351 | 11/1996 | (WO). |

OTHER PUBLICATIONS

Lai, et al. Symposium to the 9th Biennial Scientific Mtg., Asian Pacific Assoc. for the Study of the Liver—1994.
Brouwer et al., Journal of Hepatology 21 (Suppl 1) 1994, S17, Abstract No. WP2/08.
The Merck Index, 11th ed., Compound No. 8199.
Dusheiko et al., Hepatology, vol. 20, No. 4, Pt 2, 1994, Abstract No. 440.
Bodenheimer et al., Hepatology, vol. 20, No. 4, Pt 2, 1994, Abstract No. 441.
Bisceglie et al., Hepatology, vol. 16, No. 3, 1992, 649–654.
Kakyumu et al., Gastroenterology 1993: 105:507–512.
Marcellin, et al. Bailliere's Clinical Gastroenterology, vol. 8, No. 2, Jun. 1994, 233–253.
Brillanti et al., J. Hepatol 18 (Suppl 1) 1993, S101, Abstract No. T–69.
Sambataro, J. Hepatol, 18 (Suppl. 1) 1993, S167, Abstract No. T–377.
Wu et al., Antiviral Re. (Suppl 1) 1993, 165, Abstract No. 228.
Cavalletto, L. et al., Congress Proceedings from Ital. J. Gastroeterol., 25, 443–68 Abstrat at p. 452 (Venezia; Nov. 11–13, 1993).
Brillanti et al., Gastroenterology 1994: 107:812–817.
Brillanti, Hepatoogy 18 (4 Part 2) 1993, 150A, Abstract No. 375.
Lai et al., Hepatology 18 (4 Part 2) 1993, 93A, Abstract No. 146.
Chemello et al., Journal of Hepatology 21 (Suppl 1) 1994, S12, Abstract No. GS 5/29.
Package Insert for Intron A–Interferon alfa–2b Recombinant, 1992, Schering Corporation, Kenilworth, NJ.
Schvarcz et al., J. Med Virology, vol. 46 (1995) pp. 43–47.
Braconier et al., Scand J. Infectious Dis vol. 27 (1995) pp. 325–339.
Bizollon, T. et al. Revue Francaise De Castro–Enterologie Apr. 1994, No. 297 vol. XXX 429 English & French Language Versions.
Reichard et al. Journal of Hepatology, vol. 26 No. 3, Suppl: Sep. 1, 1997, 108S–111S.
Telfer et al., British Journal of Haematology, 1997, 98, 850–855.
Sherlock, S., Journal of Hepatology, 1995; 23(Suppl.2) pp. 1–2.
Sherlock, S., *ibid*, pp. 3–7.
Chemello et al., *ibid*, pp. 8–12.
Brillianti et al., *ibid*, pp. 13–16.
Schvarcz et al., *ibid*, pp. 17–21.
Bizollon et al., *ibid*, pp. 22–25.
Smith et al., *ibid*, pp. 26–31.
Main, J., *ibid*, pp. 32–36.
Panel Discussion, *ibid*, pp. 37–40.
Bellobuono, A., et al. *J. Viral Hepat.*, 1997 May, vol. 4(3): 185–91 (Abstract).
Smith, Donald B., et al, *J. of Hepatology*, 1995: vol. 23 (Suppl. 2) 26–31.
Martinot–Peignoux, Michele, et al, *Hepatology*, 1995, vol. 22 (No. 4): 1050–1056.
Schalm;Solko W., et al., *J. of Hepatology*, 1997, vol. 26: 961–966.
Lau, Johnson, Y.N., et al., *The Lancet*, Jun. 12, 1993, vol. 341: 1501–1504.
Reichard. Olle, et al, http://www.hepnet.com/nih/reich.html, Mar. 24–26, 1997 (Abstract).

*Primary Examiner*—James O. Wilson
(74) *Attorney, Agent, or Firm*—Thomas D. Hoffman; James R. Nelson

(57) ABSTRACT

There is disclosed a method for treating a patient having chronic hepatitis C infection to eradicate detectable HCV-RNA involving a combination therapy using a therapeutically effective amount of ribavirin and a therapeutically effective amount of interferon-alpha for a time period of from 20 up to 80 weeks.

10 Claims, No Drawings

COMBINATION THERAPY FOR ERADICATING DETECTABLE HCV-RNA IN PATIENTS HAVING CHRONIC HEPATITIS C INFECTION

Chronic infection with hepatitis C virus is an insidious and slow-progressing disease having a significant impact on the quality of life. It can eventually result in cirrhosis of the liver, decompensated liver disease and/or hepatocelluar carcinoma.

Alpha interferon monotherapy is commonly used to treat chronic hepatitis C infection. However, this treatment is not always effective and sometimes results in intolerable side effects related to the dosage and duration of therapy. Ribavirin has been proposed as a monotherapy treatment for chronic hepatitis C infection (Thomas et al. MSLD Abstracts, Hepatology Vol. 20, NO. 4, Pt 2, Number 440, 1994). However, this monotherapy treatment has usually been found relatively ineffective and has its own undesirable side effects. Combination therapy of alpha interferon and ribavirin has been proposed (Lai, et al. Symposium to the 9th Biennial Scientific Meeting Asian Pacific Association for the Study of the Liver. 1994). Preliminary results suggest that the combination therapy may be more effective than either monotherapy. Hayden F G, Schlepushkin A N. Combined interferon-a2, rimantadine hydrochloride, and ribavirin inhibition of influenza virus replication in vitro. *Antimicrob Agents Chemother*. 1984;25:53–57. Schvarcz R, Ando Y, S'nnerborg A, Weiland 0. Combination treatment with interferon alfa-2b and ribavirin for chronic hepatitis C in patients who have failed to achieve sustained response to interferon alone: Swedish experience. *J Hepatology*. 1995;232 (Suppl 2):17–21. Brouwer J. T, Nevens F, Michielsen P, et al. What options are left when hepatitis C does not respond to interferon? Placebo-controlled Benelux multicentre retreatment trial on ribavirin monotherapy versus combination with interferon. *J Hepatol*. 1994;212 (Suppl 1):S17. Abstract WP2/08. Chemello L, Cavalletto L, Bemardinello E, et al. Response to ribavirin, to interferon and to a combination of both in patients with chronic hepatitis C and its relation to HCV genotypes. *J Hepatol*. 1994;212 (Suppl 1):S12. Abstract GS5/29. However, no one has described methods using alpha interferon and ribavirin which eradicate HCV-RNA in any long-term, effective manner.

There is a definite need for a method for treating chronic hepatitis C infection with a combination of alpha interferon and ribavirin which eradicates HCV-RNA in any long-term, effective manner.

SUMMARY OF THE INVENTION

The present invention involves a method of treating a patient having chronic hepatitis C infection to eradicate detectable HCV-RNA comprising administering a therapeutically effective amount of ribavirin and a therapeutically effective amount of interferon-alpha for a time period of 20 to 30 weeks, such that at least about 30% of the patients having no detectable HCV-RNA at the end of said 20 to 30 week period also have no detectable HCV-RNA for at least 24 weeks after the end of said administration. Preferably, at least about 40% of the patients having no detectable HCV-RNA at the end of said 20 to 30 week period also have no detectable HCV-RNA for at least 24 weeks after the end of said administration.

In another embodiment the present invention relates to a method of treating a patient having chronic hepatitis C infection to eradicate detectable HCV-RNA comprising administering a therapeutically effective amount of ribavirin and a therapeutically effective amount of interferon-alpha for a time period of 40 to 50 weeks, such that at least about 40% of the patients having no detectable HCV-RNA at the end of said 40 to 50 week period also have no detectable HCV-RNA for at least 24 weeks after the end of said administration. Preferably, at least about 50% of the patients having no detectable HCV-RNA at the end of said 40 to 50 week period also have no detectable HCV-RNA for at least 24 weeks after the end of said administration.

Another embodiment of the invention relates to a method of treating a patient having chronic hepatitis C infection to eradicate detectable HCV-RNA comprising administering a therapeutically effective amount of ribavirin and a therapeutically effective amount of interferon-alpha for a time period of 60 to 80 weeks, such that at least about 50% of the patients having no detectable HCV-RNA at the end of said 60 to 80 week period also have no detectable HCV-RNA for at least 24 weeks after the end of said administration. Preferably, at least about 60% of the patients having no detectable HCV-RNA at the end of said 60 to 80 week period also have no detectable HCV-RNA for at least 24 weeks after the end of said administration.

One aspect of the invention involves a method of treating a patient having chronic hepatitis C infection having HCV genotype other than type 1 and having a viral load of less than or equal to 2 million copies per ml of serum as measured by HCV-RNA quantitative PCR to eradicate detectable HCV-RNA comprising administering a therapeutically effective amount of ribavirin and a therapeutically effective amount of interferon-alpha for a time period of 20 to 30 weeks, such that at least about 70% of the patients having no detectable HCV-RNA at the end of said 20 to 30 week period also have no detectable HCV-RNA for at least 24 weeks after the end of said administration. Preferably, at least about 80% of the patients having no detectable HCV-RNA at the end of said 20 to 30 week period also have no detectable HCV-RNA for at least 24 weeks after the end of said administration.

Another aspect of the invention relates to a method of treating a patient having chronic hepatitis C infection having HCV genotype other than type 1 and having a viral load of greater than 2 million copies as measured by HCV-RNA/qPCR to eradicate detectable HCV-RNA comprising administering a therapeutically effective amount of ribavirin and a therapeutically effective amount of interferon-alpha for a time period of 20 to 30 weeks, such that at least about 50% of the patients having no detectable HCV-RNA at the end of said 20 to 30 week period also have no detectable HCV-RNA for at least 24 weeks after the end of said administration. Preferably, at least about 60% of the patients having no detectable HCV-RNA at the end of said 20 to 30 week period also have no detectable HCV-RNA for at least 24 weeks after the end of said administration.

Yet another aspect of the invention involves a method of treating a patient having chronic hepatitis C infection having HCV genotype type 1 and having a viral load of less than or equal to 2 million copies as measured by HCV-RNA/qPCR to eradicate detectable HCV-RNA comprising administering a therapeutically effective amount of ribavirin and a therapeutically effective amount of interferon-alpha for a time period of 20 to 30 weeks, such that at least about 30% of the patients having no detectable HCV-RNA at the end of said 20 to 30 week period also have no detectable HCV-RNA for at least 24 weeks after the end of said administration. Preferably, at least about 40% of the patients having no detectable HCV-RNA at the end of said 20 to 30 week period also have no detectable HCV-RNA for at least 24 weeks after the end of said administration.

Still another embodiment of the invention relates to a method of treating a patient having chronic hepatitis C infection having HCV genotype type 1 and having a viral load of greater than 2 million copies as measured by HCV-RNA/qPCR to eradicate detectable HCV-RNA comprising administering a therapeutically effective amount of ribavirin and a therapeutically effective amount of interferon-alpha for a time period of 20 to 30 weeks, such that at least about 15% of the patients having no detectable HCV-RNA at the end of said 20 to 30 week period also have no detectable HCV-RNA for at least 24 weeks after the end of said administration. Preferably, at least about 20% of the patients having no detectable HCV-RNA at the end of said 20 to 30 week period also have no detectable HCV-RNA for at least 24 weeks after the end of said administration.

Preferably, the amount of ribavirin administered is firm 400 to 1200 mg per day. More preferably, the amount of ribavirin administered is from 800 to 1200 mg per day.

The interferon-alpha administered is preferably selected from interferon alpha-2a, interferon alpha-2b, a consensus interferon, a purified interferon alpha product or a pegylated interferon-alpha. More preferably, the interferon-alpha is selected from interferon alpha-2a, interferon alpha-2b, or a purified interferon alpha product and the amount of interferon-alpha administered is from 2 to 10 million IU per week on a weekly, TIW, QOD or daily basis. In a preferred embodiment, the interferon-alpha administered is interferon-alpha-2b and the amount of interferon-alpha is administered 3 million IU TIW.

Alternatively, the interferon-alpha administered is consensus interferon and the amount of interferon-alpha administered is from 1 to 20 micrograms per week on a weekly, TIW, QOD or daily basis. In another embodiment, the interferon-alpha administered is a pegylated interferon alpha-2b and the amount of interferon-alpha administered is from 0.5 to 2.0 micrograms/kilogram per week on a weekly, TIW, QOD or daily basis. Alternatively, the interferon-alpha administered is a pegylated interferon alpha-2a and the amount of interferon-alpha administered is from 20 to 250 micrograms/kilogram per week on a weekly, TIW, QOD or daily basis.

The present invention has surprisingly found that, when compared to interferon-alpha treatment alone or ribavirin alone, therapy with a combination of a therapeutically effective amount of ribavirin and a therapeutically effective amount of interferon-alpha for a time period of at least 20 to 30 weeks results in ten times more patients having no detectable HCV-RNA in their serum at least 24 weeks after termination of therapy than by either monotherapy.

DETAILED DESCRIPTION

The term "interferon-alpha" as used herein means the family of highly homologous species-specific proteins that inhibit viral replication and cellular proliferation and modulate immune response. Typical suitable alpha interferons include, but are not limited to, recombinant interferon alpha-2b such as Intron-A interferon available from Schering Corporation, Kenilworth, N.J., recombinant interferon alpha-2a such as Roferon interferon available from Hoffmann-La Roche, Nutley, N. J., recombinant interferon alpha-2C such as Berofor alpha 2 interferon available from Boehringer Ingelheim Pharmaceutical, Inc., Ridgefield, Conn., interferon alpha-n1, a purified blend of natural alpha interferons such as Sumiferon available from Sumitomo, Japan or as Wellferon interferon alpha-n1 (INS) available from the Glaxo-Wellcome Ltd., London, Great Britain, or a consensus alpha interferon such as those described in U.S. Pat. Nos. 4,897,471 and 4,695,623 (especially Examples 7, 8 or 9 thereof) and the specific product available from Amgen, Inc., Newbury Park, Calif., or interferon alpha-n3 a mixture of natural alpha interferons made by Interferon Sciences and available from the Purdue Frederick Co., Norwalk, Conn., under the Alferon Tradename. The use of interferon alpha-2a or alpha 2b is preferred. Since interferon alpha 2b, among all interferons, has the broadest approval throughout the world for treating chronic hepatitis C infection, it is most preferred. The manufacture of interferon alpha 2b is described in U.S. Pat. No. 4,530,901.

Ribavirin, 1-β-D-ribofuranosyl-1H-1,2,4-triazole-3-carboxamide, available from ICN Pharmaceuticals, Inc., Costa Mesa, Calif., is described in the Merck Index, compound No. 8199, Eleventh Edition. Its manufacture and formulation is described in U.S. Pat. No. 4,211,771.

A person suffering from chronic hepatitis C infection may exhibit one or more of the following signs or symptoms:
(a) elevated ALT,
(b) positive test for anti-HCV antibodies,
(c) presence of HCV as demonstrated by a positive test for HCV-RNA,
(d) clinical stigmata of chronic liver disease,
(e) hepatocelluar damage.

To practice the invention, alpha interferon (hereinafter α-IFN) and ribavirin are administered to the patient exhibiting one of more of the above signs or symptoms in amounts sufficient to eliminate or at least alleviate one or more of the signs or symptoms. In a preferred embodiment, the combination therapy of the invention is administered to a patient who has failed to remain HCV-RNA free after interferon-alpha monotherapy.

The ribavirin is administered to the patient in association with the α-IFN, that is, the α-IFN dose is administered during the same period of time that the patient receives doses of ribavirin. Most α-IFN formulations are not effective when administered orally, so the preferred method of administering the α-IFN is parenterally, preferably by subcutaneous, IV, or IM, injection. The ribavirin may be administered orally in capsule or tablet form in association with the parenteral administration of α-IFN. Of course, other types of administration of both medicaments, as they become available are contemplated, such as by nasal spray, transdermally, by suppository, by sustained release dosage form, etc. Any form of administration will work so long as the proper dosages are delivered without destroying the active ingredient.

Detectable HCV-RNA in the context of the present invention means that there is less than 100 copies per ml of serum of the patient as measured by quantitative, multi-cycle reverse transcriptase PCR methodology. HCV-RNA is preferably measured in the present invention by the methodology described below. This methodology is referred to herein as HCV-RNA/qPCR.

RNA is extracted from patient serum using a guaninidium thiocyanate-phenol-chloroform mister followed by ethanol-ammonium acetate precipitation. The precipitated RNA is centrifuged and the resulting pellet is dried in a Centrivap console (Labconco, Kansas City, Mo.). The dry pellet is resuspended in 30 microliters of an Rnasin (Promega Corp., Madison, Wis.), dithiothritol, and diethylpyrocarbonate-treated water mixture. Samples are kept at or below −20° C. until RNA reverse transcription (RT) and PCR.

In order to convert the entire RNA sequence into cDNA in the RT reaction, random hexadeoxyribonucleotides (Pharmacia Biotech, Piscataway, N.J.) are used as primers for the first strand cDNA synthesis. Two aliquots of 3 microliters of resuspended sample is added to 3 microliters of 100 ng/µl random primers and denaturated at 70° C., then reverse transcribed at 40° C. for one hour using M-MLV reverse transcriptase (USB, Cleveland, Ohio) in standard buffer containing 5 mM $MgCl_2$. The final RT reaction volume is 26 µl. The PCR is started immediately following the reverse transcription.

A modified version of the PCR method is performed using heat-stable Taq polymerase to amplify the cDNA. Seventy-five microliters of PCR mix is added to the entire RT reaction volume (26 µl) to a final $MgCl_2$ concentration of 1.5 mM in a total volume of 101 µl. Each 101 µl sample is then split into 50.5 µl, and a layer of mineral oil is placed on top to prevent evaporation.

The PCR cycle consists of annealing for 90 sec., extension for 90 sec., and denaturation for 90 sec., at 55° X, 74° C. and 94° C., respectively. Thermocycling samples is submitted to a final 74° C. extension for 10 minutes. Four different cycle sets are used. Bu; loading the sample in duplicate, and splitting these samples evenly after RT, there are four tubes from one sample. Each of the four tubes is given a different cycle number, enhancing sensitivity and accuracy in the quantitation process. The thermocycling efficiency will be assessed by satisfactory amplification of known copy number RNA standards included in each set of 60 tubes. Two primer sets are used for the amplification, both from the 5' untranslated region of the HCV genome. Both of these primer sets are highly conserved and detect all known subtypes of HCV. Primer set 1: upstream 5°-GTG GTC TGC GGA ACC GGT GAG T-3', downstream 5'-TGC ACG GTC TAC GAG ACC TC-3' which produced a 190 bp product. Primer set 2: upstream 5'-CTG TGA GGA ACT ACT GTC TTC-3', downstream 5'-CCC TAT CAG GCA GTA CCA CAA-3' which produced a 256 bp product.

The amplified cDNA is then electrophorised in 3% agarose gel and transferred to nylon membrane. The target DNA is detected by Southern blotting and immunostaining using a nonradioactive digoxigenin-labeled DNA probe. These procedures are performed using automated instruments for PCR thermocycling, agarose gel electrophoresis, vacuum-transfer Southern blot, hybridization, and immunostaining. Each membrane contains known copy number serially diluted standards which are used to construct standard curves for quantitative measurement of the specimen bands. Originally standard curves are made from carefully diluted HCV-RNA from transcribed clones. Radioactive incorporation studies, gel electrophoresis, and OD 260 are performed on the transcripts to determine that they are of the expected length. After the production of the RNA transcripts quantitated clone standards "pooled" standards are generated which better represent the heterogeneous nature of HCV, one would encounter in natural infection. These pools are made by combining large amounts of serum or plasma from known infected individuals. The serum/plasma pools are calibrated with PCR, against the clone transcripts and then diluted in the known PCR-negative fluids. Finally, the higher copy number samples of the pools are checked against the cDNA Quantiplex nucleic acid detection system from Chiron Inc. (Emeryville, Calif.). These "double quantitated" pools are aliquoted and saved at −70° C. Dilutions of 5,000,000, 1,000,000, 500,000, 100,000, 10,000, and 1000 copies/ml are used in each experiment.

Each Southern blot membrane is scanned into a computer using an automated scanner/densitometer, at intervals during development to determine when the standard curve is most linear. The resultant electronic images are then measured for band area and mean band density. All of the reading are standardized to integrated band density and compared to the standard curve to obtain a numerical value of viral copy number for each band.

The following clinical protocols were performed:

STUDY 1

Overall Design and Plan of the Study

This was a prospective, multicenter, randomized, double-blind, parallel-group. The study compared treatment with INTRON® A plus ribavirin to treatment with INTRON® A plus placebo for 24 weeks in patients with compensated chronic hepatitis C who had responded to one or two previous courses of alpha interferon (INTRON® A, Roferon®-A, or Wellferon®) therapy (minimum of 3 MU to a maximum of 6 MU QOD or TIW for a minimum of 20 weeks to a maximum of 18 months) and who had relapsed after the most recent course of alpha interferon therapy. Eligible patients had chronic hepatitis C confirmed by positive serum HCV-RNA, liver biopsy, and laboratory tests.

Patients were randomized to treatment with either INTRON® A plus ribavirin or INTRON® A plus placebo. The dose of INTRON® A was 3 MU SC TIW; the dose of ribavirin was 1000 or 2000 mg PO daily (based on weight) in two divided doses. Treatment group assignments were made in equal ratios by a Central Randomization Center. The randomization procedure was designed to attempt to balance the treatment groups, within and across sites, with respect to presence or absence of cirrhosis in the pretreatment liver biopsy, serum HCV-RNA/qPCR level, and HCV genotype.

Study treatment was administered for 24 weeks. The total course of the study was 48 weeks to determine long-term effect of treatment.

During treatment and posttreatment follow-up, biochemical (ALT), virological (HCV-RNA), and histological (liver biopsy) examinations were used to assess the nature and duration of response to study treatment. The primary efficacy variable was the overall response defined as loss of serum HCV-RNA/qPCR (<100 copies/mL) as measured at 24 weeks following the end of therapy associated with an improvement in posttreatment liver biopsy as measured by the Knodell Histology Activity index (HAI). Normalization of ALT was also examined as a secondary efficacy variable. The safety of the study treatments was assessed by monitoring selected laboratory parameters and by also recording and evaluating the occurrence of any adverse events.

Treatment Regimens

The study treatment regimens were either:
!INTRON® A 3 MU SC TIW plus ribavirin 1000 or 1200 mg/day PO in two divided doses for 24 weeks; or
!INTRON® A 3 MU SC TIW plus placebo matching ribavirin PO in two divided doses for 24 weeks.

Study treatment was administered for 24 weeks. The standard INTRON® A (interferon alfa-2b, recombinant) regimen for hepatitis C was administered as a fixed dose of 3 MU TIW. Each patient received instructions regarding the preparation and subcutaneous administration of INTRON® A. Ribavirin was administered twice daily, morning and evening. The dose was determined by the patient's body weight at the Entry visit. Patients weighing ≦75 kg received 1000 mg daily as two 200 mg capsules in the morning and three 200 mg capsules in the evening. Patients weighing >75 kg received 1200 mg daily as three 200 mg capsules morning and evening.

The randomization procedure was designed to balance the groups with respect to the following Baseline characteristics:

pretreatment liver histology (cirrhosis or no cirrhosis);
serum HCV-RNA/qPCR status (HCV-RNA/qPCR ≦2,000,000 or HCV-RNA/qPCR >2,000,000 copies/mL); and
HCV Genotype (1 or other). Patients with mixed genotypes (which include Type 1) will be classified as Type 1 for purposes of balancing.

Efficacy

The primary efficacy objective was comparison of the two treatment groups with respect to the overall response rate defined as loss of serum HCV-RNA/qPCR at 24 weeks following the end of therapy to an undetectable level or to a level <100 copies/mL associated with an improvement in Post treatment liver biopsy as defined by the Knodell HAI inflammation score. The following secondary efficacy Endpoints were also examined:

The secondary efficacy Endpoints:
proportions of patients with normalization of ALT at 24 weeks of follow-up;
proportions of patients with improvement in biopsy (Categories I+II+III combined scores);
changes from Baseline in the biopsy scores (Categories I+II+III combined scores);
response rates at Endpoint of treatment based on HCV-RNA/qPCR;
proportion of patients with normalization of ALT at Endpoint of treatment.
response rates at 24 weeks of follow-up based on HCV-RNA/qPCR.

Virology: Entry Status and Change from Entry

Serum HCV-RNA/qPCR testing was performed by a central laboratory. A positive HCV-RNA assay result was required at Baseline; only patients positive for HCV-RNA were eligible to participate. Repeat assays were scheduled at Weeks 4, 12, 24, and Follow-up Weeks 12 and 24.

Response was assessed as defined below:

Responder: A patient was classified as a responder at a given time point if HCV-RNA/qPCR was negative (<100 copies per mL) at that time point.

Sustained Responder: A patient was classified as a sustained responder if the patient was a responder at 24 weeks of follow-up.

Note that patients who do not meet these criteria, including patients who discontinued before the required HCV-RNA/qPCR evaluations were obtained, were classified as non-responders.

OverallResponder: Based on both serum HCV-RNA/qPCR and change in liver histology as evaluated by the Knodell HAI Inflammation Score. A patient was classified as an overall responder to treatment if he/she was a sustained responder and his/her Post treatment Knodell HAI inflammation score (sum of categories I+II+III) improved by 2 or more units relative to the Pretreatment score.

Liver Histology

Liver biopsy was required within the six months preceding patient enrollment and at Follow-up Week 24. Evaluation of the biopsies was performed by a single pathologist using the Knodell Histology Activity Score. The central pathologist was blinded with respect to patient identification, treatment group, and the time the biopsywas obtained relative to treatment (Pre- or Posttreatment). Efficacy of study treatments was assessed by comparing the degree of inflammatory activity observed at Baseline with that present at Follow-up Week 24.

RESULTS

One hundred-ninety-five patients were enrolled at 31 international centers and randomized to treatment with either INTRON® A plus ribavirin (N=98) or INTRON® A plus placebo (N=97). Three patients, two randomized to receive INTRON® A plus ribavirin and one randomized to receive INTRON® A plus placebo were not treated; thus, the all-treated groups consisted of 192 patients (96 patients each for INTRON® A plus ribavirin and INTRON® A plus placebo). Two of the three patients were not treated because they did not wish to continue, the third because the protocol criteria were not met. All discussions of efficacy and safety in this report are based on data for the all-treated groups.

Efficacy

The objectives of this study were to compare INTRON® A plus ribavirin with INTRON® A plus placebo with respect to the overall response rate and the virologic response rate (based on HCV-RNA (qPCR). The primary efficacy variable for the study is the overall response rate.

The conclusion from this regarding efficacy are as follows:

Combining ribavirin with INTRON® A can dramatically increase the proportion of patients who eradicate HCV-RNA and have significant reduction in hepatic inflammation.

The End of Follow-up overall response rate is a composite of the loss of serum HCV-RNA(qPCR) and change in liver histology at end of follow-up (24 weeks following the end of treatment). A patient was classified as an overall responder if HCV-RNA(PCR) was negative at the 24 week posttreatment evaluation and the posttreatment Knodell HAI inflammation score (sum of categories I+II+III) had improved by 2 or more units relative to the pretreatment score. The End of Follow-up virologic response, histologic response, and overall response rates are summarized in Tables 1, 2, and 3.

End of Follow-up HCV-RNA Response

Sustained Loss of HCV-RNA 24 Weeks Following the End of Treatment

The proportion of patients with eradication of HCV-RNA in the serum 24 weeks following the end of treatment was tenfold greater (p<0.001) in the group of patients treated with the combination of INTRON® A plus ribavirin compared to those receiving INTRON® A monotherapy. Table 1 summarizes the End of Follow-up patient response as indicated by serum HCV-RNA.

TABLE 1

End of Follow-up Serum HCV-RNA: Proportion of Patients with
Eradication of HCV-RNA at 24 Week Following the End of Treatment.

|  | Number (%) of Patients | | |
|---|---|---|---|
| Patient Response Status | INTRON ® A plus Ribavirin | INTRON ® A plus Placebo | p value |
| All Treated | 50/96 (52) | 5/96 (5) | <0.001 |
| 95% Confidence Interval for each treatment: | | | |
| for difference between treatments: | 42%–62% | 1%–10% | |
| | | 4%–58% | |
| Responders at End of Treatment[c] | 49/80 (61) | 5/41 (12) | |

Pre- and Posttreatment biopsies were available for 81% (78/96) of the patients treated with INTRON® A plus ribavirin and for 77% (74/96) of those patients who received INTRON® A plus placebo. Table 2 summarizes the effect of treatment on hepatic inflammation for patients with both pre- and posttreatment liver biopsy results. As with the sustained loss of HCV-RNA replication, the proportion of patients with improvement in liver inflammation was significantly greater (p<0.001) in patients receiving combination therapy compared to those receiving INTRON® A monotherapy.

TABLE 2

End of Follow-up Liver Histology: Improvement in Liver Histology
24 Weeks Following the End of Treatment Based on the Knodell HAI
(I + II + III) Score.

|  | Number (%) of Patients[b] | | |
|---|---|---|---|
| Patient Status | INTRON A plus Ribavirin (n = 78) | INTRON A plus Placebo (n = 74) | p value[c] |
| Improved Biopsy[d] | 49 (51) | 30 (31) | <0.001 |

[a]
[b]Patients with both pre- and posttreatment biopsy.
[c]Fisher's Exact test.
[d]Change from pretreatment to posttreatment in the Knodell Histological Index (HAI) score (sum of I + II + III) categorized as a decrease of 2 or more from pretreatment.

Overall Response

When the study was designed, it was recognized that because liver biopsy is an invasive procedure that it would be unlikely that posttreatment liver biopsies would be obtained for all patients. Therefore, the protocol and statistical analysis plan specified that the analysis for overall response would be based on data for all treated patients and will be estimated by a maximum likelihood method (MLE) for patients whose overall response status could not be determined, ie, patients with negative HCV-RNA and missing (posttreatment) biopsy evaluations. The protocol also specified that an additional analysis would be performed on patients with both pretreatment and posttreatment biopsy results (ie, patients with complete data). The overall response is summarized in Table 3 based on the following analyses:

maximum likelihood estimate (MLE);

patients with complete data (results for both pre- and posttreatment biopsy);

patients with missing data (either or both HCV/biopsy) treated as failures.

TABLE 3

Overall Response Rate.

| Data Analyzed | INTRON ® A plus Ribavirin | INTRON ® A plus Placebo | p value[b] |
|---|---|---|---|
| Maximum likelihood estimate | 43% | 5% | <0.001 |
| Patients with complete data[c] | 39/78 (50%) | 4/74 (5%) | <0.001 |
| Treat missing as failures[d] | 39/96 (41%) | 4/98 (4%) | <0.001 |

[a]
[b]Fisher's exact test.
[c]Complete data = pre- and posttreatment biopsy results.
[d]Patients who had either virology or biopsy data missing or both were counted as failures.

As would be anticipated from individual results for effect of treatment on eradication of HCV-RNA at end of follow-up and improvement in hepatic inflammation, the overall response rate in the INTRON® A plus ribavirin treatment group was significantly greater (<0.001), with a 10 to 14 fold improvement, than that observed in the INTRON® A plus placebo group for all methods of evaluation.

Logistic regression analysis was done on all Baseline demographic variables and disease characteristics. The only Baseline statistically significant characteristics predictive of End of Follow-up sustained response were genotype other than 1 and viral load ≦2 million.

For number of viral copies (≦2 million, >2 million), the difference was statistically significant in favor of higher response rates in patients with ≦2 million copies (Table 4).

When genotype and Baseline virus load are combined, a hierarchy of response is observed. Those patients with genotype other than 1 and Baseline virus load ≦2 million copies had the best End of Follow-up response; those patients with genotype 1 and >2 million copies had the poorest End of Follow-up response.

TABLE 4

Disease Characteristics vs Sustained Response: All-Treated Patients.

|  | Number (%) of Patients | |
|---|---|---|
| Disease Characteristic[b] | INTRON A plus ribavirin (n = 96) | INTRON A plus Placebo (n = 96) |
| HCV-RNA/gPCR | | |
| ≦2 million | 24/36 (67) | 5/29 (17) |
| ≧2 million | 26/60 (43) | 0/67 (0) |
| HCV Genotype[c] | | |
| 1 | 16/53 (30) | 2/53 (4) |
| Other | 34/43 (79) | 3/19 (7) |
| Genotype/Baseline HCV-RNA/gPCR | | |
| Other/≦2 million copies | 15/16 (93) | 3/14 (21) |
| Other/>2 million copies | 18/27 (67) | 0/29 (0) |
| 1/≦2 million copies | 8/20 (40) | 0/15 (0) |
| 1/>2 million copies | 7/33 (21) | 0/38 (0) |

[a]
[b]At entry, patients were stratified by number of viral copies (≦2 million, >2 million), genotype (1 or other), and cirrhosis (present or absent).

STUDY 2

By basically the same methodology as described above in Study 1, a second Study 2 was also conducted. The results are summarized below.

Efficacy

The End of Follow-up overall response rate is a composite of the loss of serum HCV-RNA(qPCR) and change in liver histology at End of Follow-up (24 weeks following the end of treatment). A patient was classified as an overall responder if HCV-RNA(PCR) was negative at the 24 week posttreatment evaluation and the posttreatment Knodell HAI inflammation score (sum of categories I+II+III) had improved by 2 or more units relative to the pretreatment score. The End of Follow-up virologic response, histologic response, and overall response rates are summarized in Tables 5, 6, and 7.

End of Follow-up HCV-RNA Response

Sustained Loss of HCV-RNA 24 Weeks Following the End of Treatment

The proportion of patients with eradication of HCV-RNA in the serum 24 weeks following the end of treatment was ten-fold (p<0.001), in the group of patients treated with the combination of INTRON® A plus ribavirin compared to those receiving INTRON® A monotherapy. Table 5 summarizes the End of Follow-up patient response as indicated by serum HCV-RNA.

TABLE 5

End of Follow-up Serum HCV-RNA: Proportion of Patients with Eradication of HCV-RNA at 24 Weeks Following the End of Treatment.

| | Number (%) of Patients | | |
|---|---|---|---|
| Patient Response Status | INTRON A plus Ribavirin | INTRON A plus Placebo | p value |
| All-treated Patients | 34/77 (44) | 3/76 (4) | <0.001 |
| 95% Confidence Interval for each treatment: | | | |
| for difference between treatments | 33%–56% | 0%–8% | |
| | | 28%–52% | |
| Responders at End of Treatment[c] | 34/54 (83) | 3/32 (9) | |

End of Follow-up Liver Histology

Improvement in Liver Histology 24 Weeks Following the End of Treatment Based on Knodell Histological Activity Index (HAI) Scores (I+II+III)

Pre- and Posttreatment biopsies were available for 79% (61/77) of the patients treated with INTRON® A plus ribavirin and for 84% (64/76) of those patients who received INTRON® A plus placebo. Table 6 summarizes the effect of treatment on hepatic inflammation for patients with both pre- and posttreatment liver biopsy results. As with the sustained loss of HCV-RNA replication, the proportion of patients with improvement in liver inflammation was significantly greater (p<0.001) in patients receiving combination therapy compared to those receiving INTRON® A monotherapy.

TABLE 6

End of Follow-up Liver Histology: Improvement in Liver Histology 24 Weeks Following the End of Treatment Based on the Knodell HAI (I + II + III) Score.

| | Number (%) of Patients[b] | | |
|---|---|---|---|
| Patient Status | INTRON A plus Ribavirin (n = 61) | INTRON A plus Placebo (n = 64) | p value[c] |
| Improved Biopsy[d] | 38 (49) | 27 (36) | <0.001 |

[a]
[b]Patients with both pre-and posttreatment biopsy.
[c]Fisher's Exact test.
[d]Change from pretreatment to posttreatment in the Knodell Histological Index (HAI) score (sum of I + II + III) categorized as a decrease of 2 or more from pretreatment.

Overall Response

The overall response is summarized in Table 7 based on the following analyses:

maximum likelihood estimate (MLE);

patients with complete data (results for both pre- and posttreatment biopsy);

patients with missing data (either or both HCV-RNA/ biopsy) treated as failures.

TABLE 7

Overall Response Rate.

| Data Analyzed | INTRON A plus Ribavirin | INTRON A plus Placebo | p value[b] |
|---|---|---|---|
| ML estimate | 36.5% | 2.7% | <0.001 |
| Patients with complete data[c] | 25/61 (41.0) | 2/64 (3.1%) | <0.001 |
| Treat missing as failures[d] | 25/77 (32.5) | 2/76 (2.6%) | <0.001 |

[a]
[b]Fisher's Exact test.
[c]Complete data = pre- and posttreatment biopsy results.
[d]Patients who had either virology or biopsy data missing or both were counted as failures.

As would be anticipated from individual results for effect of treatment on eradication of HCV-RNA at End of Follow-up and improvement in hepatic inflammation, the overall response rate in the INTRON A plus ribavirin group is significantly greater (p<0.001) with a 10–14 fold improvement over that observed with INTRON A plus placebo groups for all methods of evaluation.

Logistic regression analysis was done on all Baseline demographic variables and disease characteristics. The only Baseline statistically significant characteristic predictive of End of Follow-up sustained response was genotype other than 1.

For number of viral copies (≦2 million, >2 million), there was a numerical difference in favor of higher response rates in patients with ≦2 million copies (Table 8). When genotype and Baseline virus load are combined, a hierarchy of response is observed. Those patients with genotype other than 1 and Baseline virus load ≦2 million copies had the best End of Follow-up response; those patients with genotype 1 and >2 million copies had the poorest End of Follow-up response.

TABLE 8

Disease Characteristics vs Sustained Response: All-Treated Patients.

|  | Number (%) of Patients | |
| --- | --- | --- |
| Disease Characteristic[b] | INTRON ® A plus ribavirin (n = 77) | INTRON ® A plus Placebo (n = 76) |
| HCV-RNA/gPCR | | |
| ≦2 million | 6/9 (67) | 1/12 (8) |
| >2 million | 28/68 (41) | 2/64 (3) |
| HCV Genotype[c] | | |
| 1 | 12/46 (28) | 1/42 (2) |
| Other | 21/31 (68) | 2/34 (6) |

TABLE 8-continued

Disease Characteristics vs Sustained Response: All-Treated Patients.

|  | Number (%) of Patients | |
| --- | --- | --- |
| Disease Characteristic[b] | INTRON ® A plus ribavirin (n = 77) | INTRON ® A plus Placebo (n = 76) |
| Genotype/Baseline HCV-RNA/gPCR | | |
| Other/≦2 million copies | 4/4 (100) | 0/3 (0) |
| Other/>2 million copies | 1/27 (62) | 2/31 (6) |
| 1/≦2 million copies | 2/5 (40) | 1/9 (11) |
| 1/>2 million copies | 11/39 (28) | 0/32 (0) |

Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

---

What is claimed is:

1. A method of treating a patient having chronic hepatitis C infection having HCV genotype 1 and having a viral load of greater than 2 million copies/mL of serum HCV-RNA as measured by HCV-RNA/qPCR to eradicate detectable HCV-RNA comprising administering a therapeutically effective combination of ribavirin and interferon-alpha for a time period of at least 24 weeks wherein the patient has fewer than about 100 copies/mL of serum HCV-RNA at the end of said period and also has less than about 100 copies/mL of serum HCV-RNA for at least 24 weeks after the end of said period.

2. The method of claim 1, wherein the amount of ribavirin administered is from about 400 to about 1200 mg per day.

3. The method of claim 1, wherein the amount of ribavirin administered is from about 800 to about 1200 mg per day.

4. The method of claim 1, wherein the interferon-alpha administered is selected from interferon alpha-2a, interferon alpha-2b, a consensus interferon, a purified interferon alpha product or a pegylated interferon-alpha.

5. The method of claim 2, wherein the amount of the interferon-alpha administered is selected from interferon alpha-2a, interferon alpha-2b or a purified interferon alpha product and the amount of the interferon-alpha administered is from about 2 to about 10 million IU per week on a weekly, TIW, QOD or daily basis.

6. The method of claim 3, wherein the amount of the interferon-alpha administered is about 3 million IU TIW.

7. The method of claim 2, wherein the interferon-alpha administered is interferon alpha-2b and the amount of the interferon-alpha administered is about 3 million IU TIW.

8. The method of claim 2, wherein the interferon-alpha administered is consensus interferon and the amount of the interferon-alpha administered is from about 1 to about 20 micrograms per week on a weekly, TIW, QOD or daily basis.

9. The method of claim 2, wherein the interferon-alpha administered is pegylated interferon alpha-2b and the amount of the interferon-alpha administered is from about 0.5 to about 2.0 micrograms/kilogram per week on a weekly, TIW, QOD or daily basis.

10. The method of claim 2, wherein the interferon-alpha administered is pegylated interferon alpha-2a and the amount of the interferon-alpha administered is from about 20 to about 250 micrograms/kilogram per week on a weekly, TIW, QOD or daily basis.

* * * * *

SEQUENCE LISTING (1) GENERAL INFORMATION:

(iii) NUMBER OF SEQUENCES: 4

(2) INFORMATION FOR SEQ ID NO: 1:

(i) SEQUENCE CHARACTERISTICS:
      (A) LENGTH: 22 base pairs
      (B) TYPE: nucleic acid
      (C) STRANDEDNESS: single
      (D) TOPOLOGY: linear (ii) MOLECULE TYPE: DNA (oligonucleotide)

(xi) SEQUENCE DESCRIPTION: SEQ ID NO: 1:

GTGGTCTGCG GAACCGGTGA GT        22

(2) INFORMATION FOR SEQ ID NO: 2:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: DNA (oligonucleotide)

(xi) SEQUENCE DESCRIPTION: SEQ ID NO: 2:

TGCACGGTCT ACGAGACCTC        20

(2) INFORMATION FOR SEQ ID NO: 3:

(i) SEQUENCE CHARACTERISTICS:
      (A) LENGTH: 21 base pairs
      (B) TYPE: nucleic acid
      (C) STRANDEDNESS: single -continued

```
        (D) TOPOLOGY: linear (ii) MOLECULE TYPE: DNA (oligonucleotide)

(xi) SEQUENCE DESCRIPTION: SEQ ID NO: 3:

CTGTGAGGAA CTACTGTCTT C                                                21

(2) INFORMATION FOR SEQ ID NO: 4:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 4:

CCCTATCAGG CAGTACCACA A                                                21
```